(12) United States Patent
Yamamoto et al.

(10) Patent No.: US 8,596,557 B2
(45) Date of Patent: *Dec. 3, 2013

(54) PEST CONTROL AEROSOL SPRAYER

(75) Inventors: Kazunori Yamamoto, Hatsukaichi (JP); Katsuo Sugimaru, Hatsukaichi (JP)

(73) Assignee: Fumakilla Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/562,812

(22) Filed: Jul. 31, 2012

(65) Prior Publication Data

US 2012/0312897 A1 Dec. 13, 2012

Related U.S. Application Data

(62) Division of application No. 12/918,117, filed as application No. PCT/JP2009/053797 on Feb. 24, 2009, now Pat. No. 8,393,554.

(30) Foreign Application Priority Data

Feb. 25, 2008 (JP) ................................ 2008-042943

(51) Int. Cl.
 *B05B 7/32* (2006.01)
(52) U.S. Cl.
 USPC ............ 239/337; 239/414; 239/536; 239/549
(58) Field of Classification Search
 USPC ......... 239/337, 405, 414, 493, 536, 548, 552, 239/549
 See application file for complete search history.

(56) References Cited

U.S. PATENT DOCUMENTS

| | | | |
|---|---|---|---|
| 3,628,733 A | 12/1971 | Kahn | |
| 4,583,692 A * | 4/1986 | Sheffler et al. | ................ 239/405 |
| 4,834,967 A | 5/1989 | Locicero | |
| 5,735,465 A | 4/1998 | Laforcade | |
| 6,149,077 A | 11/2000 | Pohler | |

(Continued)

FOREIGN PATENT DOCUMENTS

| | | |
|---|---|---|
| JP | 62-132803 A | 6/1987 |
| JP | 2001-233390 A | 8/2001 |

(Continued)

OTHER PUBLICATIONS

International Search Report dated May 26, 2009 issued in parent International Application. No. PCT/JP2009/053797.

(Continued)

*Primary Examiner* — Steven J Ganey
(74) *Attorney, Agent, or Firm* — Holtz, Holtz, Goodman & Chick, PC

(57) ABSTRACT

A pest control aerosol sprayer that is free from giving rise to a fire or a burn in its storage or use, includes a pressure-tight container receiving therein a noxious insect behavioral inhibitor of which an active ingredient is HFC-152a acting also as both a propellant and refrigerant. The pressure-tight container has at its top a valve having a stem, and the stem has an injection hole therein that can be opened with the stem forced down. A head cap is attached to a top of the pressure-tight container and is provided with a spray nozzle and an inflow port in which the stem of the valve in the pressure-tight container is fitted. The head cap has an injection passage leading from the inflow port to the spray nozzle.

3 Claims, 4 Drawing Sheets

(56) References Cited

U.S. PATENT DOCUMENTS

| | | | |
|---|---|---|---|
| 6,419,168 B1 | 7/2002 | Thieleke et al. | |
| 6,817,493 B1* | 11/2004 | Parsons et al. | 239/548 |
| 2003/0220296 A1 | 11/2003 | Besser et al. | |
| 2007/0092545 A1 | 4/2007 | Bale | |
| 2011/0000980 A1* | 1/2011 | Yamamoto et al. | 239/337 |

FOREIGN PATENT DOCUMENTS

| | | |
|---|---|---|
| JP | 2004-168948 A | 6/2004 |
| JP | 2005-270089 A | 10/2005 |
| JP | 2006-122319 A | 5/2006 |
| WO | WO 2006/101882 A2 | 9/2006 |

OTHER PUBLICATIONS

International Preliminary Report on Patentability dated Oct. 5, 2010 (in English) in parent International Application No. PCT/JP2009/053797.

Extended European Search Report (EESR) dated Mar. 11, 2011 (in English) in counterpart European Application No. 09714350.7.

Siegemund et al.: "Fluorine Compounds, Organic": Ullmann's Encyclopedia of Industrial Chemistry; (Jan. 1, 2005); pp. 1, 7-10.

Environmental Protection Agency Federal Register: "1,1-Difluoroethane, Tolerance Exemption"; vol. 61, No. 146; (Jul. 29, 1996); pp. 39351-39353.

* cited by examiner

PEST CONTROL AEROSOL SPRAYER

CROSS REFERENCE TO RELATED APPLICATIONS

This application is a Divisional of U.S. application Ser. No. 12/918,117, filed Sep. 7, 2010, now U.S. Pat. No. 8,393,554 which is based upon and claims the benefit of priority from International Application No. PCT/JP2009/053797, filed Feb. 24, 2009, which is further based on and claims the benefit of priority from prior Japanese Patent Application No. 2008-042943, filed Feb. 25, 2008, the entire contents of all of which are incorporated herein by reference.

TECHNICAL FIELD

The present invention relates to a pest control aerosol sprayer, i.e., an aerosol sprayer for exterminating a noxious insect, comprising a pressure-tight container containing therein a noxious insect behavioral inhibitor and a head cap attached to a top of the pressure-tight container and provided with a spray nozzle, for spraying the noxious insect behavioral inhibitor in the pressure-tight container through the spray nozzle of the head cap to ex-terminate the noxious insect.

BACKGROUND ART

A pest control aerosol sprayer has so far consisted of a hermetically closed pressure-tight container and a head cap attached to a top of the pressure-tight container.

The pressure-tight container is provided at a top center thereof with a valve including a vertically movable stem, the container containing an insectifuge therein. The insectifuge contained in the pressure-tight container is a liquid mixture of an insecticide and a liquefied petroleum gas (LPG) as its propellant.

Also, the head cap is provided with a spray nozzle directed forwards and on its rear side with an operating button.

And, in an operation of the pest control aerosol sprayer, pressing the operating button on the head cap by a user pushes down the stem of the valve in the pressure-tight container to cause the insectifuge contained in the pressure-tight container to be sprayed under its internal gas pressure via the stem of the valve in the pressure-tight container and forwards through and out of the spray nozzle on the head cap.

Such a pest control aerosol sprayer, however, in which the insectifuge contained in the pressure-tight container has an insecticide mixed therein has had several restrictions. Thus, since the insecticide exerts an adverse effect not a little on the human body, its use in the vicinity of a kitchen where there are foodstuff and tableware likely infested with noxious insects gives rise to the problem that the insecticide in the insectifuge sprayed comes to adhere to foodstuff and tableware. Or its use in a room where there is a baby or small infant does the problem that the insecticide comes to be sprayed on the baby or small infant. Thus, in the vicinity of a kitchen where there are foodstuffs and tableware or in a room where there is a baby or small infant it has been the actual fact that the pest control aerosol sprayer is refrained from using or is not used at all.

Accordingly, instead of an insectifuge using an insecticide exerting an adverse effect on the human body, it has become known in recent years to use a pest control aerosol sprayer using a noxious insect behavioral inhibitor having a refrigerating effect and little adversely affecting the human body. To cite an example, as shown in JP 2004-168948 A a noxious insect behavioral inhibitor containing dimethyl ether and water is used which is caused to attach to a noxious insect to refrigerate the noxious insect, thereby terminating its behavior, i.e., to kill it by its paralysis.

Such a pest control aerosol sprayer, however, has the problem firstly that the pressure-tight container to contain the noxious insect behavioral inhibitor cannot be made of normal steel but must be made of aluminum to avoid its rusting, corrosion or the like; an aluminum made pressure-tight container is high in price, making the pest control aerosol sprayer highly expensive. Secondly, the problem is had that dimethyl ether used in the noxious insect behavioral inhibitor has a chemical property that it is exceptionally high in flammability, giving rise in its storage and use to the problem of a fire or burn. Other than dimethyl ether, materials which have been used for the noxious insect behavioral inhibitor have their flammability as strong as dimethyl ether, much likely to lead to the problem of a fire or burn.

Also, a pest control aerosol sprayer using an insectifuge having mixed therein an insecticide, not a noxious insect behavioral inhibitor, is likely to lead to the problem of a fire or burn because of the use as its propellant of a liquefied petroleum gas that is strong in flammability.

Accordingly, it is an object of the present invention to provide a pest control aerosol sprayer for exterminating noxious insects which is free from bringing about such problems, in particular the problem of a fire or burn that is its most important matter.

DISCLOSURE OF THE INVENTION

The present invention provides in a first aspect thereof a pest control aerosol sprayer, which comprises: a pressure-tight container containing therein a noxious insect behavioral inhibitor of which an active ingredient is an alternative for chlorofluorocarbon acting also as both a propellant and refrigerant, the pressure-tight container having at its top a valve provided with a stem and in the stem with an injection hole that can be opened with the stem forced down; and a head cap attached to a top of the pressure-tight container and provided with a spray nozzle and an inflow port in which the stem of the valve in the pressure-tight container is fitted, the head cap being formed therein with an injection passage leading from the inflow port to the spray nozzle.

The present invention provides in a second aspect thereof a pest control aerosol sprayer according to the first aspect mentioned above, in which the alternative for chlorofluorocarbon that is an active ingredient of the noxious insect behavioral inhibitor is HFC-152a.

The present invention provides in a third aspect thereof a pest control aerosol sprayer according to the first aspect mentioned above, in which the alternative for chlorofluorocarbon that is an active ingredient of the noxious insect behavioral inhibitor is HFO-1234yf.

The present invention provides in a fourth aspect thereof a pest control aerosol sprayer according to the first aspect mentioned above, in which the alternative for chlorofluorocarbon that is an active ingredient of the noxious insect behavioral inhibitor is HFO-1234ze.

The present invention provides in a fifth aspect thereof a pest control aerosol sprayer according to any one of the first to fourth aspects mentioned above, in which the injection passage formed in the head cap is provided with a pressure reducer means for lowering the pressure of a gas prior to its reaching the spray nozzle.

The present invention provides in a sixth aspect thereof a pest control aerosol sprayer according to the fifth aspect mentioned above, in which the pressure reducer means includes injection passages bifurcated into and provided with at least two spray nozzles whereby the pressure of the gas is lowered prior to its reaching a spray nozzle.

According to the present invention, using a noxious insect behavioral inhibitor of which an active ingredient is an alternative for chlorofluorocarbon acting also as both a propellant and refrigerant allows refrigerating a noxious insect and terminating the behavior of the noxious insect, i.e., killing the noxious insect on its paralyzing, thereby exterminating the noxious insects, without adversely affecting the human body. And, using as the active ingredient of the noxious insect behavioral inhibitor, an alternative for chlorofluorocarbon which has the chemical property that it is very low in flammability, eliminates the problem such as of a possible fire or burn in its storage or use, and thus serves to provide extremely safe products of a pest control aerosol sprayer.

Also, if the noxious insect behavioral inhibitor is used of which an active ingredient is an alternative for chlorofluorocarbon such as HFC-152a, HFO-1234yf or HFO-1234ze whose gas pressure is extremely high, the pest control aerosol sprayer equipped with a pressure reducer mean in the injection passage of the head cap allows the pressure reducer means to lower the pressure of gas prior to its reaching a spray nozzle, thereby rendering the noxious insect behavioral inhibitor in the form of a mist whose small drops are of a desired particle size for shooting successfully from a spray nozzle.

BEST MODES FOR CARRYING OUT THE INVENTION

Mention is made of a pest control aerosol sprayer as one form of implementation of the present invention.

Figure 1:
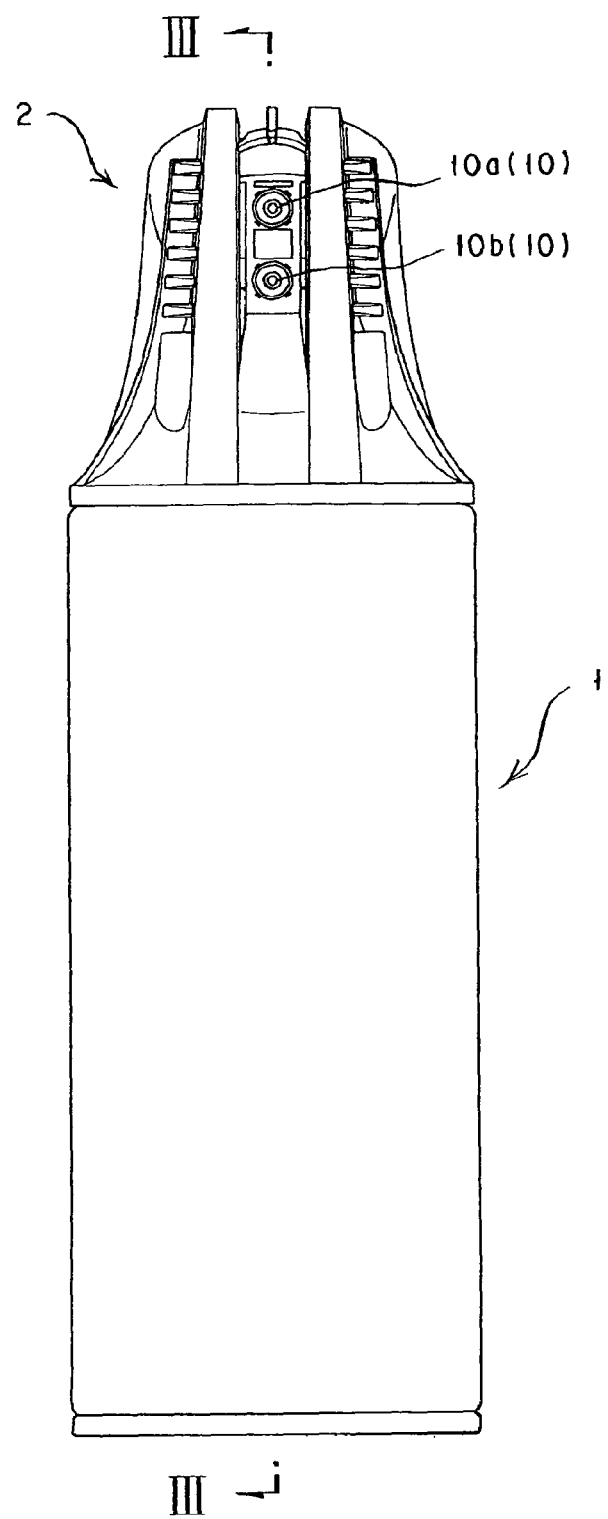
FIG. 1 is a front view of a pest control aerosol sprayer according to the present invention.
Figure 2:
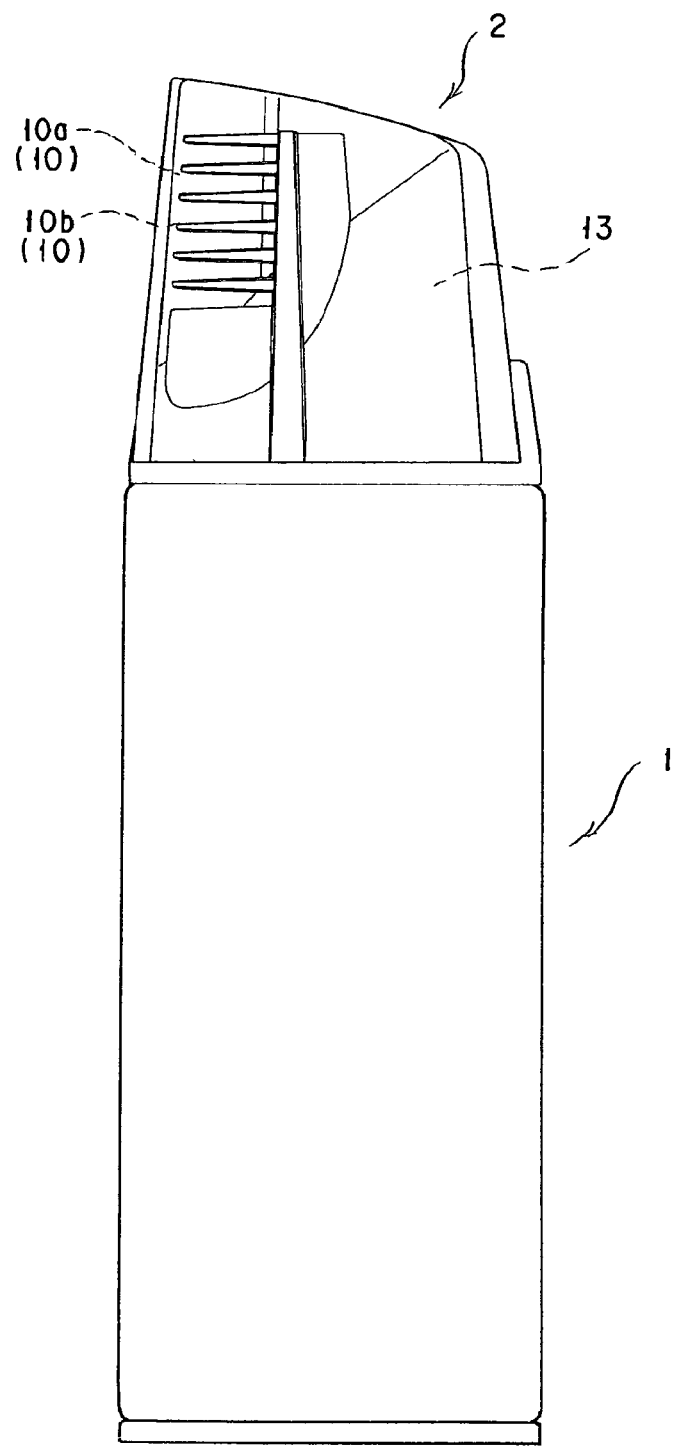
FIG. 2 is a side view of the pest control aerosol sprayer according to the present invention.

The pest control aerosol sprayer as shown in FIGS. 1 and 2 consists of a hermetically closed pressure-tight container 1 and a head cap 2 attached to a top of the pressure-tight container 1.

Figure 3:
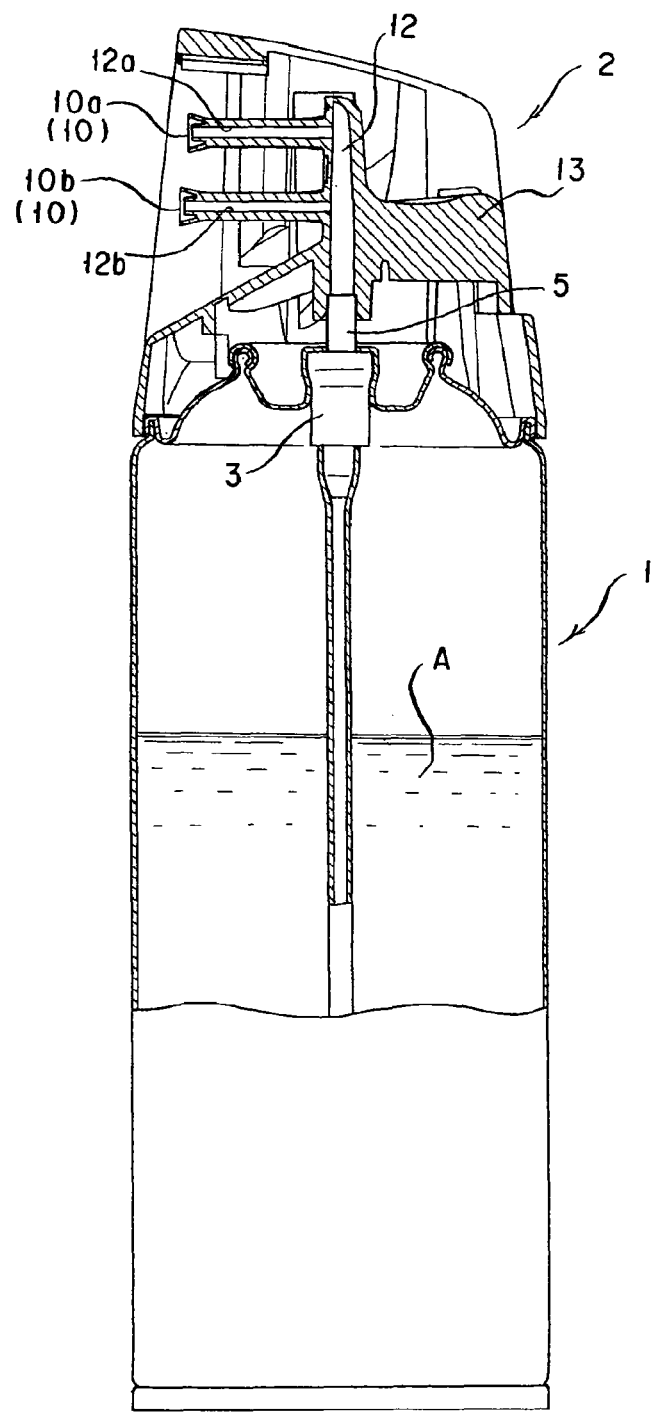
FIG. 3 is a cross sectional view taken along the line in FIG. 1.
Figure 4:
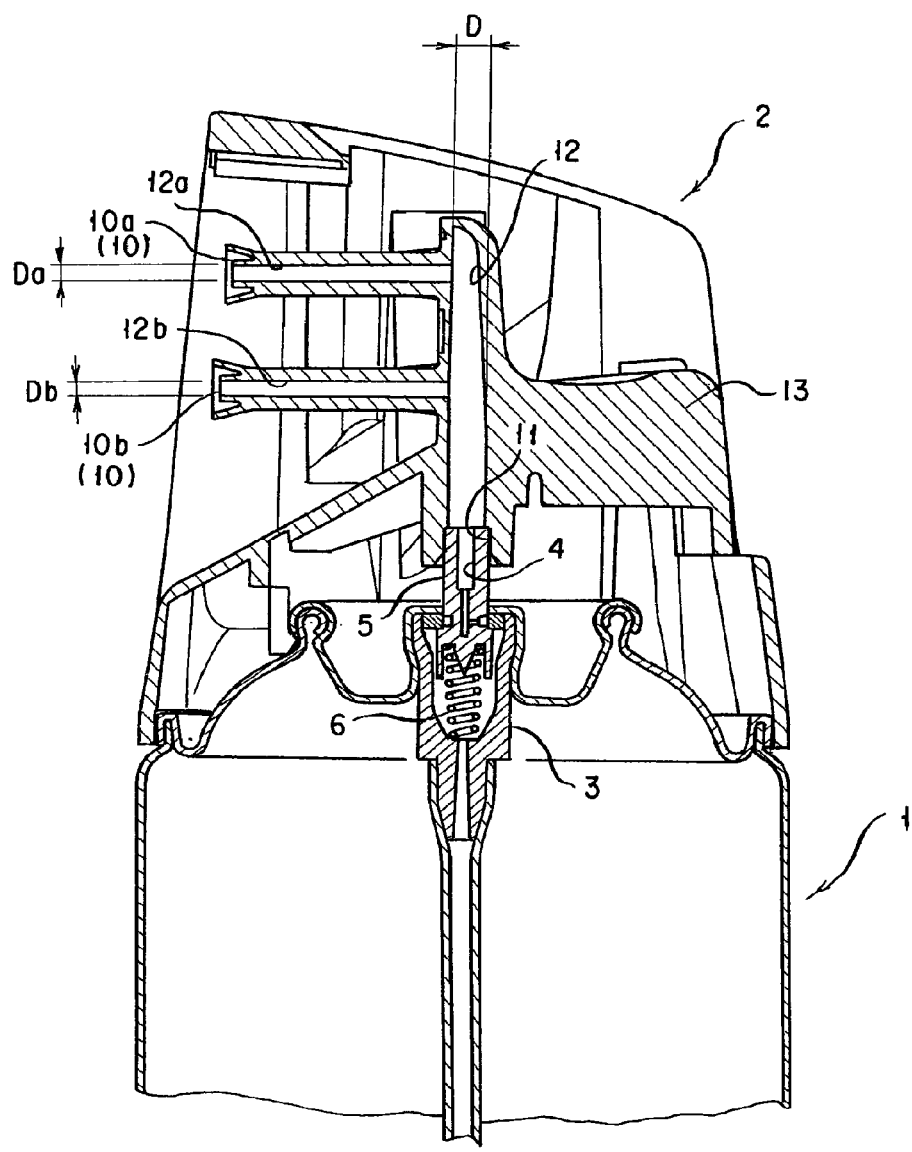
FIG. 4 is an enlarged cross sectional view illustrating the neighborhood of a head cap.

As shown in FIGS. 3 and 4, the pressure-tight container 1 is provided in an upper and central area thereof with a valve 3 in which a vertically movable stem 5 having an injection hole 4 is forced upwards by a spring 6. The valve 3 is so designed that moving the stem 5 downwards causes the injection hole 4 in the stem 5 to be opened. The pressure-tight container 1 is made of steel but it does not intend to be limited to being so.

And, the pressure-tight container 1 contains a noxious insect behavioral inhibitor A which has an alternative for chlorofluorocarbon acting as an active ingredient and also as a propellant and refrigerant. The alternatives for chlorofluorocarbon include hydrofluorocarbon and hydrofluoroolefin and these alternatives for chlorofluorocarbon have a chemical property that their flammability is very low. And, as the alternative for chlorofluorocarbon in this form of implementation is used HFC-152a (1,1-difluoroethane) (chemical formula: $CHF_2CH_3$; CAS No. 75-37-6) that is a kind of hydrofluorocarbon. The content of HFC-152a in the noxious insect behavioral inhibitor A will be described later herein. While hydrofluorocarbon for use may not necessarily be HFC-152a but may be HFC-134a (chemical formula: $CH_2FCF_3$; CAS No. 811-97-2) as another kind thereof, it should most preferably be HFC-152a, taking into account use conditions, operations and effects. However, there are very suitable ones other than hydrofluorocarbons such as HFC-152a. For example, they are as hydrofluoro-olefins, HFO-1234yf (2,3,3,3-tetrafluoropropene) (chemical formula: $CF_3CF\!=\!CH_2$; CAS No. 754-12-1) and HFO-1234ze (1,3,3,3-tetrafluoropropene) (chemical formula: $CF_3CH\!=\!CFH$; CAS No. 1645-83-6). Such HFO-1234yf and HFO-1234ze have a global warming potential (GWP) lower than that of HFC-152a and also have a chemical property such that they are lower in flammability than HFC-152a. Moreover, HFO-1234ze is not flammable at all and thus nonflammable. From these reasons it is desirable, too, to use HFO-1234yf and HFO-1234ze as alternatives for chlorofluorocarbon and especially the latter well, taking into account their chemical properties.

The head cap 2 is provided with a spray nozzle 10 facing forward and in a lower and central area thereof with an inflow port 11 in which the stem 5 of the valve 3 in the pressure-tight container 1 is fitted. The head cap 2 is formed with an injection passage 12 extending to the spray nozzle 10 from the inflow port 11. The head cap 2 is further provided on its rear side with an operating button 13.

Instead of the operating button 13 provided on the rear side of the head cap 2, there may be provided a trigger lever on the lower side of the spray nozzle 10 that is a front side of the head cap 2. Also, instead of facing forwards, the spray nozzle 10 may be made to face upwards.

And, as shown in FIG. 4 the head cap 2 is equipped in its internally formed injection passage 12 with a pressure reducer means for decreasing the pressure of a gas before it reaches the spray nozzle 10. In a specific example illustrated as the pressure reducer means, the injection passage 12 is bifurcated into an upper injection passage 12a and a lower injection passage 12b and the spray nozzle 10 is mounted to the end of each of the upper and lower injection passages 12a and 12b. By means of bifurcating the injection passage 12, the pressure of the gas is caused to decrease before it reaches the spray nozzle 10. For such an injection passage 12, let it be here that the injection passage 12 prior to bifurcation is of a diameter D of 3 to 4 mm, the upper injection passage 12a is of a diameter Da of 1.5 mm and the lower injection passage 12b is of a diameter Db of 1.8 mm. Making the size (diameter Da) of the upper injection passage 12 a little smaller than the size (diameter Db) of the lower injection passage 12b in this manner allows rendering conditions of spraying from the upper and lower spray nozzles 10a and 10b even and sufficient.

Also, while the pressure reducer means provided in the injection passage 12 bifurcates the injection passage 12, it does not intend to be limited to doing so. The pressure reducer means may bifurcate or divide the injection passage 12 into three or more passage parts provided with three or more spray nozzles 10. Further, instead of bifurcating the injection passage 12, the injection passage 12 may be provided midway therein with a pressure reducing or decompressing chamber that is larger in cross section than the injection passage 12. As the pressure reducer means, however, bifurcating the injection passage 12 is the simplest and quite plain to facilitate manufacturing.

And, in operation of the pest control aerosol sprayer shown, pressing the operating button 13 in the head cap by a user forces down the stem 5 of the valve 3 to open the injection hole 4 in the stem 5 whereby the noxious insect behavioral inhibitor A contained in the pressure-tight container 1 is forced by its propellant action, namely under gas pressure to flow from the injection hole 4 of the stem 5 in the pressure-tight container 1 into the inflow port 11 and the injection passage 12 in the head cap 2, then splitting to flow into the upper and lower injection passages 12a and 12b which are bifurcated into as the pressure reducer means in the injection passage 12. Flowing through the upper and lower injection passages 12a and 12b, the noxious insect behavioral inhibitor A is then sprayed forwards from the upper and lower spray nozzles 10a and 10b. And, if the noxious insect behavioral inhibitor A getting into the air adheres to an noxious insect, the insect will in a moment be refrigerated and terminated of its behavior, i.e., be paralyzed and killed, thus exterminated.

It is noted here that a noxious insect behavioral inhibitor A having an alternative for chlorofluorocarbon acting as an active ingredient and also as a propellant and refrigerant, specifically a noxious insect behavioral inhibitor A having HFC-152a acting as an active ingredient is considerably high in gas pressure, having a gas pressure as high as 4 to 5 kgf/cm$^3$ or more (at 25° C.), compared with liquid petroleum gas (LPG) usually used as propellant, which has a gas pressure of 2.8 kgf/cm$^3$ (at 25° C.). Another alternative for chlorofluorocarbon has a high gas pressure as well as this. Consequently, spraying the noxious insect behavioral inhibitor A in an ordinary manner causes the noxious insect behavioral inhibitor A to be too high in gas pressure at the spray nozzle 10 and to be sprayed in the form of a mist of exceedingly small drops or particles, which renders the efficiency of adherence of the noxious insect behavioral inhibitor to noxious insects low and fails to achieve satisfactory behavioral inhibiting effect. Accordingly, in the present invention there is provided a pressure reducer means as a pressure dividing mechanism that bifurcates the injection passage 12 formed in the head cap 2, thereby enabling the pressure of the gas when sprayed from the spray nozzle 10 to be lowered to some degree. This allows the noxious insect behavioral inhibitor A when sprayed through the spraying nozzle 10 to be sprayed in the form of coarse mist particles, thereby increasing the efficiency of its adherence to noxious insects and enhancing their refrigerating effect, thus achieving the satisfactory behavioral inhibiting effect. And, the noxious insect behavioral inhibitor A when sprayed has an average particle size of 60 to 200 μm, preferably 70 to 150 μm. In comparison, an insectifuge having an ordinary insecticide mixed therein in a conventional pest control aerosol sprayer has an average particle size of around 20 μm. And, with the average particle size less than 60 μm, the particles come to soar and scatter along surfaces of noxious insects, and adherence of the noxious insect behavioral inhibitor A to noxious insects is very poor.

Mention is next made of the content of HFC-152a in the noxious insect behavioral inhibitor A.

HFC-152a itself acting also as a propellant and refrigerant, it can be used alone in and as the noxious insect behavioral inhibitor A, although a separate substance or substances can be mixed therewith.

In this case, HFC-152a is contained at a proportion of 75% or more. In other words, the content of HFC-152a is 75 to 100%.

And, substances that can be mixed in HFC-152a are dimethyl ether, normal butane, isobutan, propane and their mixed gases as liquefied petroleum gases. But, being flammable, they if mixed much become high in flammability. Thus, when mixed with them, HFC-152a must be of a content of no less than 75%. If HFC-152a having a content of less than 75% is sprayed at a fire origin or the like, it is likely to lead to a backfire causing a serious problem such as of a fire or burn. Also, while hydrocarbon normal pentane, isopentane, normal hexane or the like having the carbon number of 5 or 6 which is high in boiling point may be mixed, it is high in flammability, requiring its mixing ratio to be set low. Besides, it is possible to mix a compressed gas such as of nitrogen, air or carbon dioxide.

Mention is further made of the content of other than HFC-152a in the noxious insect behavioral inhibitor A. For example, HFO-1234ze with the aforementioned flammability and likely backfiring problem taken into account can have its content reduced compared with HFC-152a. However, since reducing its content down to less than 50% leads again to the problem, the content must be 50% or more. In other words, HFO-1234ze needs to be contained at a proportion of 50 to 100%.

Further, the noxious insect behavioral inhibitor A may have an insecticide a little intermixed therewith for the purpose of a lethal or repellent effect. Such insecticides may, for example, be pyrethroid insecticidal components such as methofluthrin (trade name: Eminence), d1, d-T80-allethrin (trade name: Pynamin Forte), phthalthrin (trade name: Neopynamin), d-T80-phthalthrin (Neopynamine Forte), d, d-T98-prallethrin (trade name; Etoc), d, d-T98 prallethrin (trade name: 98 Etoc), d-T80-resmethrin (trade name: Chrysron Forte), transfluthrin (trade name: Biothrin), imiprothrin (trade name: Prone), etofenprox (trade name: Torebon), cyphenothrin (trade name: Gokilaht), d, d-T-cyphenothrin (trade name: Gokilaht S), empenthrin (trade name: Paperthrin), permethrin (trade name: Xmin), phenothrin (trade name: Sumithrin) and pyrethrin (trade name: Chrysanthemum Expel), organic phosphoric insecticidal component such as fenitrothion (trade name: Sumithion) and marathion (trade name: Marathon) and carbamate insecticidal components such as propoxur (trade name: Baygon) and culverin (trade name: NAG). For natural essential oils can be cited citronella oil, thyme oil, peppermint oil, lavender oil, coriander oil, cedarwood oil, fennel oil, chamomile oil, cinnamon oil, pimento oil, geranium oil, cumin oil, Japanese peppermint oil, clove oil, hiba oil and lemon grass oil. These components can be used singly or on mixing two or more of them, depending on their uses. Such an insecticidal liquid if incorporated should have a content of 0.0001 to 2 weight/volume % such as not to adversely affect the human body.

Also, as a solvent it is desirable to use 2,3-dihydrodecafluoropentane (Mitsubishi-Du Pont Fluorochemicals, Co. Ltd., trade name: Vertrel XF) or 1,1-difluoroethane (Sumitomo 3M, Co. Ltd., trade name: <Novec>HFE), which is a nonflammable solvent. By using such a nonflammable solvent, it is possible to provide a pest control aerosol sprayer that is extremely low in dangerousness leading to an explosion or flashing. Further, these solvents have a low boiling point such as to volatilize at the normal temperature of a room without remaining and without leaving dirt of such as a mark of spraying when the sprayer is used indoors. Moreover, being high in permeability when attached to a noxious insect and also having themselves a refrigerating effect, a solvent such as 2,3-dihydrodecafluoropentane or 1,1-difluoroethane further enhances the refrigerating effect on noxious insects and serves to exterminate noxious insects yet more effectively Also, using a solvent that is high in both attaching perineability and choking effect on noxious insects serves to exterminate noxious insects still more effectively. For such solvents can be cited, for example, aliphatic, aromatic and cycloaliphatic hydrocarbons, alcohols such as ethanol, isopropyl alcohol and methanol, ester, vegetable oils, animal oils and water. Among them, an aliphatic hydrocarbon is excellent in effects in that by refrigerating at the time of spraying it is solidified and iced, conducing to considerably high low-temperature retaining effect. However, being hard to volatilize, it has the possibility that it leaves dirt of a mark of spraying. The solvent is therefore set in at a content of not more than 10% by volume to get rid of dirt by spray marking.

The pest control aerosol sprayer according to the present invention allows its favorable use indoors because of the property that it leaves no residue of the noxious insect behavioral inhibitor A in an sprayed area. Noxious insects that can be effectively targeted thereby may be cockroaches such as *Blattella germanica, Periplaneta fuliginosa, Periplaneta americana, Periplaneta brunnea Burmeister* and *Periplaneta japonica*, spiders, centipedes, ants and stinkbugs. These noxious insects, of course, include also flying insects including flies such as *Musca domenstica, Fannia canicularis, Sarcophagidae, Aldrichina grahami, Drosophila melanogaster*, Psychodidae and Phoridae, mosquitoes such as *Culex pipiens pallens* and *Aedes albopictus*, and flying insects such as bees. The pest control aerosol sprayer of the present invention also exhibits a control or repelling effect on pyrethroid resistant noxious insects.

The pest control aerosol sprayer according to the present invention can be used anywhere, i.e., in a variety of places including not only a general household including a kitchen where there are foodstuff and tableware and a room where there is a baby or small infant, but also a restaurant, a hospital and the like, and will not be restricted by place of use.

Mention is next made of test examples of the present invention, although the invention does not intend to be limited to them.

Test Example 1 relates to back-fire tests for the aerosol sprayer using various gases. Specifically, aerosol sprayers loaded with various gases acting as both propellant and refrigerant were prepared. And, after these aerosol sprayers were immersed in a thermostatic bath at 25° C. for 1 hour, each of them was arranged with the flame, as a fire origin, of an ignited burner so that the spray nozzle of its head cap and the flame lied horizontally in the same height. And, each gas was sprayed from the spray nozzle of the head cap in the aerosol sprayer for 5 seconds towards the flame as the fire origin to check if there was a backfire. This was repeated a plurality of times. Here, the fire origin was spaced from the spray nozzle at a distance of 15 cm and at a distance of 60 cm. Results of the test are shown in Table 1 below.

TABLE 1

| Name of Gas | 15 cm distant from Fire Origin | 60 cm distant from Fire Origin |
|---|---|---|
| HFC-152a (100%) | Not Backfired | Not Backfired |
| HFC-134a (100%) | Not Backfired | Not Backfired |
| LPG (100%) | Backfired | Backfired |
| dimethyl ether (100%) | Backfired | Backfired |
| isopentane (50%) and LPG (50%) | Backfired | Backfired |

As the test results, it is shown that with each of LPG, dimethyl ether, and a mixture of isopentane and LPG, there was a backfire for both 15 cm and 60 cm distant from the fire origin. Moreover, the mixture of isopentane and LPG gave rise to a large flame. In contrast to these, with each of HFC-152a and HFC-134a there was no backfire for each of 15 cm and 60 cm distant from the fire origin. It is thus seen that HFC-152a and HFC-134a as alternatives for chlorofluorocarbon are extremely low in flammability.

Further, HFO-1234ze as another alternative for chlorofluorocarbon was also subjected to the same backfire tests as for HFC-152a and HFC-134a in Text Example 1 mentioned above. Results of the test are shown in Table 2.

TABLE 2

| Name of Gas | 15 cm distant from Fire Origin | 60 cm distant from Fire Origin |
|---|---|---|
| HFO-1234ze (100%) | Not Backfired | Not Backfired |

In the results of this test, it is shown as in the aforementioned backfire test that with HFO-1234ze, too, there was no backfire for each of 15 cm and 60 cm distant from the fire origin. It is thus seen that HFO-1234ze as an alternative for chlorofluorocarbon is also extremely low in flammability.

In Test Example 2, aerosol sprayers using HFC-152a as an alternative for chlorofluorocarbon were tested on its content. This, too, relates to back-fire tests. Specifically, aerosol sprayers loaded with HFC-152a alone and mixtures of HFC-15a with LPG or dimethyl ether (in varied mixture ratio) were prepared. And, after these aerosol sprayers were immersed in a thermostatic bath at 25° C. for 1 hour, each of them was arranged with the flame, as a fire origin, of an ignited burner so that the spray nozzle of its head cap and the flame lied horizontally in the same height. And, each gas was sprayed from the spray nozzle of the head cap in the aerosol sprayer for 5 seconds towards the flame as the fire origin to check if there was a backfire. This was repeated a plurality of times. Here, the fire origin was spaced from the spray nozzle at a distance of 15 cm. Results of the test are shown in Table 3 below.

TABLE 3

| Proportion of HFC-152a (%) | Name of Mixed Gas | 15 cm distant from Fire Origin |
|---|---|---|
| 100% | | Not Back-fired |
| 75% | LPG | Not Back-fired |
| 50% | LPG | Back-fired |
| 25% | LPG | Back-fired |
| 75% | dimethyl ether | Not Back-fired |
| 50% | dimethyl ether | Back-fired |
| 25% | dimethyl ether | Back-fired |

As the test results, it is shown that with each of HFC-152a alone and a mixture of HFC-152a at its mixing ratio of 75% with LPG or dimethyl ether, there was no backfire. However, with mixtures of HFC-152a at mixing ratios of 50% and 25% with LPG or dimethyl ether, there was a backfire. From these, it is seen that HFC-152a if its mixing ratio is set at 75 to 100% in its content is reduced in flammability to enhance the safety.

Further, HFO-1234ze as another alternative for chlorofluorocarbon was also tested on its content as in Text Example 2 above. Results of the test are shown in Table 2. Specifically, aerosol sprayers loaded with HFO-1234ze alone and mixtures of HFO-1234ze with LPG or dimethyl ether (in varied mixture ratio) were prepared. And, after these aerosol sprayers were immersed in a thermostatic bath at 25° C. for 1 hour, each of them was arranged with the flame, as a fire origin, of an ignited burner so that the spray nozzle of its head cap and the flame lied horizontally in the same height. And, each gas was sprayed from the spray nozzle of the head cap in the aerosol sprayer for 5 seconds towards the flame as the fire origin to check if there was a backfire. This was repeated a plurality of times. Here, the fire origin was spaced from the spray nozzle at a distance of 15 cm. Results of the test are shown in Table 4 below.

TABLE 4

| Proportion of HFO-1234ze (%) | Name of Mixed Gas | 15 cm distant from Fire Origin |
|---|---|---|
| 100% | | Not Back-fired |
| 75% | LPG | Not Back-fired |
| 50% | LPG | Not Back-fired |

TABLE 4-continued

| Proportion of HFO-1234ze (%) | Name of Mixed Gas | 15 cm distant from Fire Origin |
|---|---|---|
| 75% | dimethyl ether | Not Back-fired |
| 50% | dimethyl ether | Not Back-fired |

As the test results, it is shown that with each of HFO-1234ze alone and mixtures of HFO-1234ze at its mixing ratios of 75% and 50% with LPG or dimethyl ether, there was no backfire. From this, it is seen that HFO-1234ze if its mixing ratio is set at 50 to 100% in its content is reduced in flammability to enhance the safety. Also, HFO-1234ze itself being expensive, its mixing with LPG or dimethyl ether makes it possible to furnish them less expensively. Note further that this leaves the flammability low and gives rise to no problem whatsoever on safety.

In Test Example 3, modes of spraying from the spray nozzle 10 in the head cap 2 were examined. This is to examine the refrigerating and behavioral inhibiting effects on a noxious insect by a noxious insect behavioral inhibitor A which is sprayed from the spray nozzle 10. Specifically, a wooden flooring was prepared on which a glass ring (having a diameter of 9 cm and a height of 6 cm) was placed. Then, a rod having a diameter of 3 mm is inserted between the wooden flooring and the glass ring to form a clearance between them so that sprayed liquid does not collect inside of the glass ring. And, one female adult of *Periplaneta fuliginosa* is introduced inside of the glass ring. On the other hand, two different head caps were prepared, one provided with a single spray nozzle 10 and the other provided with a pressure reducer means comprising an upper and a lower spray nozzle 10a and 10b. And, using them, the noxious insect behavioral inhibitor A is sprayed for 3 seconds toward the *Periplaneta fuliginosa* from a distance of 50 cm therefrom, and the state of the *Periplaneta fuliginosa* thereafter (possible knockdown after 2 minutes and after 1 hour and fatality after 24 hours) is observed. Further, the minimum temperatures of a target area of spraying are measured. And, the room temperature is 25° C., and the noxious insect behavioral inhibitor A is HFC-152a alone (100%). The two head caps 2, the one with the single spray nozzle 10 and the other with the two spray nozzles 10, are made to spray substantially at a identical rate of spraying. Test results are shown in Table 5 below.

TABLE 5

| | | | | Biological test (n = 10) | | |
|---|---|---|---|---|---|---|
| | | Average | Rate of | Minimum | Knockdown rate | | Fatality |
| Spray state | | particle size (μm) | spray (g/sec) | temperature (° C.) | after 2 minutes | after 1 hour | after 24 hours |
| Single spray nozzle (1.5 mm diameter) | Fine mist | 57 | 3.7 | −38.6 | 90% | 40% | 10% |
| Two spray nozzles Upper nozzle (1.5 mm diameter) Lower nozzle (1.8 mm diameter) | Coarse mist | 97 | 3.6 | −58.7 | 100% | 100% | 100% |

The test results indicate that the head cap provided with two spray nozzles 10, i.e., equipped with a pressure reducer means as a pressure dividing mechanism that bifurcates the injection passage 12 to reduce the pressure of gas to some degree as it is sprayed from the cap, makes the sprayed mist coarser and the average mist particle size larger, and further makes the minimum temperature at the target area of spraying lower, than with the head cap having a single spray nozzle. This increases the efficiency of adherence of the noxious insect behavioral inhibitor A on a noxious insect and enhances the refrigerating effect, thereby achieving satisfactory noxious insect behavioral inhibiting effects. Note in this connection that with the head cap with a single spray nozzle alone, gas pressure is excessive, making mist drops finer and making their adherence on the insect inferior; as a result, spraying in a short period has failed to achieve satisfactory noxious insect behavioral inhibiting effects. Moreover, an excessively energetic spray may have driven the noxious insect to fly off.

Also, in Test Example 3, noxious insect behavioral inhibitors containing HFO-1234ze alone (100%), at a content of 75% and at a content of 50% were examined. What is mixed is dimethyl ether. Test results are shown in Table 6 below.

TABLE 6

| | HFO-1234ze content (%) | Name of mixed gas (%) | Spray state | Average particle size (μm) | Rate of spray (g/sec) | Min. temp. (° C.) | Biological test (n = 10) Knockdown rate after 2 minutes | Knockdown rate after 1 hour | Fatality after 24 hours |
|---|---|---|---|---|---|---|---|---|---|
| Two spray nozzles Upper nozzle (1.5 mm diameter) Lower nozzle (1.8 mm diameter) | 100% | None | Coarse mist | 120 | 4.33 | −53.7 | 100% | 100% | 60% |
| | 75% | di-methyl ether (25%) | Coarse mist | 115 | 3.75 | −52.6 | 100% | 100% | 100% |
| | 50% | di-methyl ether (25%) | Coarse mist | 109 | 3.52 | −52.7 | 100% | 100% | 100% |

From these test results it is seen, too, that the head cap provided with two spray nozzles 10, i.e., equipped with a pressure reducer means as a pressure dividing mechanism that bifurcates the injection passage 12 to reduce to some degree the pressure of gas as it is sprayed from the cap, makes the sprayed mist coarser and the average mist particle size larger, and further makes the minimum temperature at the target area of spraying lower. This increases the efficiency of adherence of the noxious insect behavioral inhibitor A on a noxious insect and enhances the refrigerating effect, thereby achieving satisfactory noxious insect behavioral inhibiting effects. It is further seen that ones with HFO-1234ze at 75% and 50% achieve still higher behavioral inhibiting effects.

What is claimed is:

1. A pest control aerosol sprayer, comprising:
a pressure-tight container which receives therein a noxious insect behavioral inhibitor of which an active ingredient is an alternative for chlorofluorocarbon acting also as both a propellant and refrigerant, the pressure-tight container having at a top thereof a valve provided with a stem, the stem having an injection hole that is openable when the stem is forced down; and
a head cap which is attached to a top of the pressure-tight container and which is provided with a spray nozzle and an inflow port in which the stem of the valve in the pressure-tight container is fitted, the head cap including an injection passage leading from the inflow port to the spray nozzle;
wherein the alternative for chlorofluorocarbon that is the active ingredient of the noxious insect behavioral inhibitor is HFC-152a, the HFC-152a being contained at a proportion of no less than 75% and being mixed with liquefied petroleum gas or dimethyl ether.

2. A pest control aerosol sprayer, comprising:
a pressure-tight container which receives therein a noxious insect behavioral inhibitor of which an active ingredient is an alternative for chlorofluorocarbon acting also as both a propellant and refrigerant, the pressure-tight container having at a top thereof a valve provided with a stem, the stem having an injection hole that is openable when the stem is forced down; and
a head cap which is attached to the top of the pressure-tight container and which is provided with a spray nozzle and an inflow port in which the stem of the valve in the pressure-tight container is fitted, the head cap including an injection passage leading from the inflow port to the spray nozzle;
wherein the alternative for chlorofluorocarbon that is the active ingredient of the noxious insect behavioral inhibitor is HFO-1234yf, the HFO-1234yf being contained at a proportion of no less than 50% and being mixed with liquefied petroleum gas or dimethyl ether.

3. A pest control aerosol sprayer, comprising:
a pressure-tight container which receives therein a noxious insect behavioral inhibitor of which an active ingredient is an alternative for chlorofluorocarbon acting also as both a propellant and refrigerant, the pressure-tight container having at a top thereof a valve provided with a stem, the stem having an injection hole that is openable when the stem is forced down; and
a head cap which is attached to a top of the pressure-tight container and which is provided with a spray nozzle and an inflow Port in which the stem of the valve in the pressure-tight container is fitted, the head cap including an injection passage leading from the inflow port to the spray nozzle;
wherein the alternative for chlorofluorocarbon that is the active ingredient of the noxious insect-behavioral inhibitor is HFO-1234ze, the HFO-12324ze being contained at a proportion of no less than 50% and being mixed with liquified petroleum gas or dimethyl ether.

\* \* \* \* \*

UNITED STATES PATENT AND TRADEMARK OFFICE
CERTIFICATE OF CORRECTION

PATENT NO.       : 8,596,557 B2
APPLICATION NO.  : 13/562812
DATED            : December 3, 2013
INVENTOR(S)      : Kazunori Yamamoto It is certified that error appears in the above-identified patent and that said Letters Patent is hereby corrected as shown below:

In the Claims

Column 12, Claim 3, Line 17:

replace "HFO -12324ze" with --HFO -1234ze--.

Signed and Sealed this
Twenty-fifth Day of February, 2014

Michelle K. Lee
*Deputy Director of the United States Patent and Trademark Office*